(12) United States Patent
Marsing et al.

(10) Patent No.: US 8,641,989 B2
(45) Date of Patent: Feb. 4, 2014

(54) TISSUE SUBSTRATE HOLDING DEVICE

(76) Inventors: Jacquelyn D. Marsing, Salt Lake City, UT (US); Lynn Marsing, Salt Lake City, UT (US)

(*) Notice: Subject to any disclaimer, the term of this patent is extended or adjusted under 35 U.S.C. 154(b) by 0 days.

(21) Appl. No.: 13/572,422

(22) Filed: Aug. 10, 2012

(65) Prior Publication Data

US 2013/0039820 A1    Feb. 14, 2013

Related U.S. Application Data

(60) Provisional application No. 61/522,785, filed on Aug. 12, 2011.

(51) Int. Cl.
| *B01L 3/02* | (2006.01) |
| *B01L 3/00* | (2006.01) |
| *F25B 19/00* | (2006.01) |
| *B23Q 3/00* | (2006.01) |

(52) U.S. Cl.
USPC ............. 422/547; 422/521; 62/51.1; 269/309

(58) Field of Classification Search
USPC ................................................ 422/547, 521
See application file for complete search history.

(56) References Cited

U.S. PATENT DOCUMENTS

| 4,751,828 | A |   | 6/1988  | Coulter et al. |
| 5,080,869 | A | * | 1/1992  | McCormick ................... 422/547 |
| 5,188,347 | A | * | 2/1993  | Hunnell et al. ............... 269/258 |
| 5,550,033 | A | * | 8/1996  | Krumdieck ................. 435/40.52 |
| 5,776,298 | A | * | 7/1998  | Franks ........................... 156/390 |
| 5,983,991 | A | * | 11/1999 | Franks .......................... 165/80.1 |
| 6,199,623 | B1 | * | 3/2001 | Franks .......................... 165/80.1 |
| 6,536,219 | B2 | * | 3/2003 | Peters ................................ 62/62 |
| 7,059,139 | B1 |   | 6/2006  | Marsing et al. |
| 7,179,424 | B2 | * | 2/2007 | Williamson et al. .......... 422/536 |
| 7,237,392 | B2 |   | 7/2007  | Marsing et al. |
| 2010/0223935 | A1 | * | 9/2010 | Donndelinger ................ 62/51.1 |

* cited by examiner

*Primary Examiner* — Jill Warden
*Assistant Examiner* — Brittany Fisher
(74) *Attorney, Agent, or Firm* — Brinks Gilson & Lione; Ryan L. Marshall

(57) ABSTRACT

A substrate holding device is disclosed for use in histological studies. The device includes a tapered groove surface for retaining a tissue substrate. The device may be used with a cryogenic procedure.

18 Claims, 3 Drawing Sheets

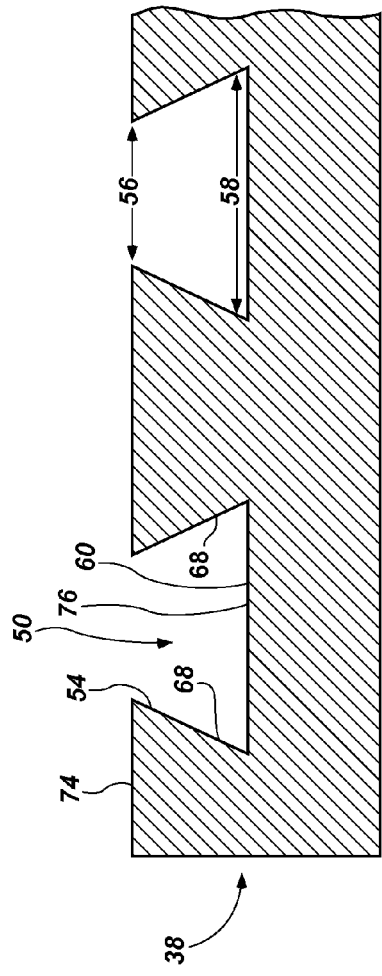
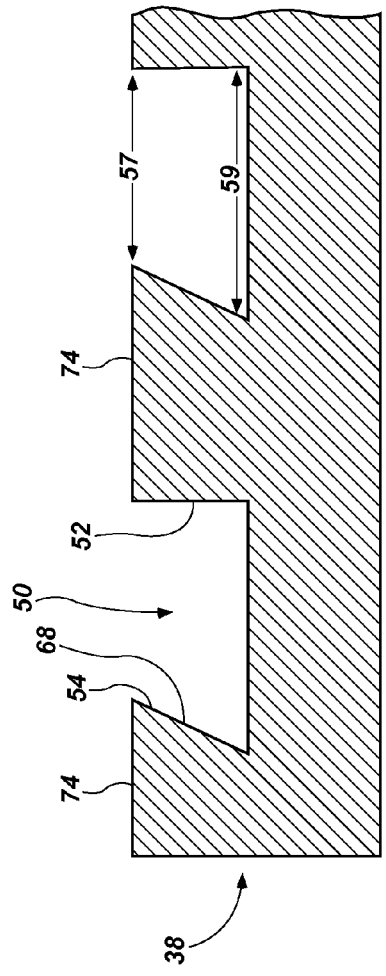
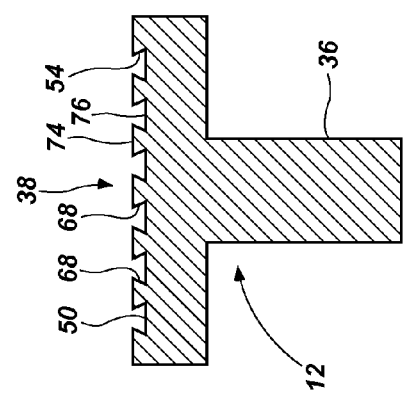
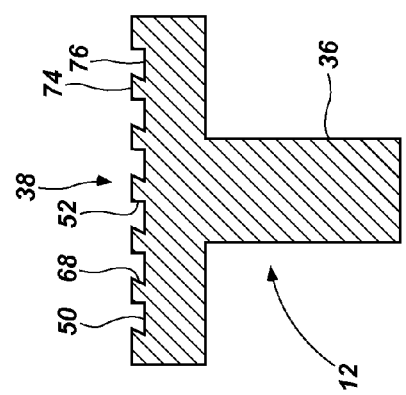

TISSUE SUBSTRATE HOLDING DEVICE

REFERENCE TO EARLIER FILED APPLICATION

The present application claims the benefit of the filing date under 35 U.S.C. §119(e) of Provisional U.S. Patent Application Ser. No. 61/522,785, filed Aug. 12, 2011; which is hereby incorporated by reference in its entirety.

BACKGROUND

There are numerous methods for preparing tissue samples for histological study. Typically, tissue samples are removed from a patient, processed, and then examined by a qualified health care professional such as a pathologist. Proper mounting and retention of the tissue sample on a substrate holding device can play an important role in accurate, reliable examination by the medical professional.

In cryogenic histological studies, for example, tissue samples can be mounted onto a tissue retaining device in an embedding media and frozen. A number of devices exist for retaining the tissue. A common problem, however, is the tendency of the frozen tissue sample to become dislodged from the retaining device during the cutting process with a cryostat microtome. There is a need, therefore, for a tissue retaining device that more securely retains a tissue sample.

SUMMARY

In one aspect, a substrate holding device is disclosed including a stem and a grooved face having a plurality of ridges and furrows forming tapered grooves. In some embodiments, the substrate holding device has a plurality of tapered edges wherein each tapered edge is between a ridge and an adjoining furrow. In some embodiments, each furrow adjoins an adjacent ridge by a tapered edge. In some embodiments, the substrate holding device includes a plurality of nontapered edges wherein each nontapered edge is between a ridge and an adjoining furrow. In some embodiments, each furrow adjoins a first adjacent ridge by a tapered edge and a second adjacent ridge by a nontapered edge.

In another aspect, a substrate holding device is disclosed including a stem and a grooved face having a plurality of tapered grooves. In some embodiments, each tapered groove further comprises a furrow adjoining first and second ridges. In some embodiments, the width of the tapered groove at the top of the first and second ridges adjoining a furrow is less than the width of the tapered groove in the bottom of the furrow. In some embodiments, the width of the tapered grooves is greater at the top of the groove than at the bottom of the groove.

In another aspect, a substrate holding device for retaining frozen tissue samples is disclosed including a stem and a tissue mounting face substantially perpendicular to the stem, the tissue mounting face further comprising a plurality of tapered grooves configured to retain a mounting medium. In some embodiments, the grooves are tapered to be wider at the bottom of the groove than the width of the top of the groove. In some embodiments, the mounting medium is a solid when cooled to a temperature less than 0° C. In some embodiments, the plurality of grooves form concentric circles. In some embodiments, the plurality of grooves are parallel to one another. In some embodiments, at least some of the plurality of grooves are perpendicular to other grooves. In some embodiments the stem is of the form selected from the group consisting of: round, square, and rectangle.

DETAILED DESCRIPTION

While the terminology used in this application is standard within the art, the following definitions of certain terms are provided to assure clarity.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Patients undergoing diagnosis or treatment for disease often require histological and pathological evaluation of tissue samples. A number of tissue sampling techniques are required to assist the medical professional for diagnosis and treatment of various diseases, including cryogenic techniques. For example, the Mohs technique was developed as one method in which a surgeon monitors the success of surgery to remove cancerous dermal tissue using cryogenic fixation of a tissue sample. Other techniques involving cryogenic fixation include: cyrofixation, immunohistochemistry (IHC), and the like.

In the drawings:

FIGS. 1A and 1B are a side elevational view of different embodiments of substrate holding devices.

FIGS. 2A and 2B are expanded side elevational views of the embodiments of FIGS. 1A and 1B.

Figure 4:
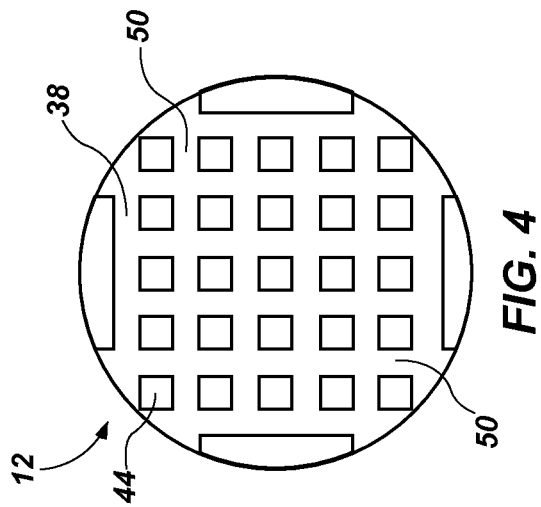
FIG. 4 is a top perspective view of the embodiments of FIGS. 1A, 1B, 2A, and 2B.

Referring to FIGS. 1A and 2A, the substrate holding device 12 is shown with a stem portion 36 and a grooved face 38 made up of a plurality of tapered grooves 50. The tapered grooves have a plurality of ridges 74 and furrows 76 where a top portion 54 of the ridge 74 overhangs a furrow 76 forming a tapered edge 68. Thus, the width of a groove is smaller at the top of the ridges 56 than the width of the groove at the bottom of the ridges (at the bottom of the furrow) 58. The tapered edge 68 spans the height between the top of a ridge 54 and the bottom of a furrow 60. The combination of ridges and furrows operate as a plurality of tapered grooves to grip and retain a tissue sample (not shown) or mounting medium (also not shown) such as a gel or fluid frozen to immobilize the tissue sample onto the substrate holding device 12.

The stem portion of the substrate holding device may have various forms including, but not limited to, round and cylindrical, square and rectangular, oval and the like. The stem can be shaped and made to a variety of lengths and widths or diameters so that it may be adapted to fit with an variety of cryostats.

In some embodiments, such as those shown in FIGS. 1A, 2A, 3, and 4, ridges 74 adjoining a common furrow 76 both overhang that furrow. In some embodiments, only one of two ridges adjoining a common furrow overhangs that furrow (as shown in FIGS. 1B and 2B). In such embodiments, a nontapered edge 52 spanning one ridge and the furrow is substantially perpendicular (or perpendicular in some embodiments) to the grooved face 38, and a tapered edge 68 spans a second ridge to the furrow. The width of a groove is smaller at the top of the ridges 57 than the width of the groove at the bottom of the ridges (at the bottom of the furrow) 59. The tapered edge 68 and nontapered edge 52 span the height between the top of a ridge 54 and the bottom of a furrow 60 but on opposite sides of a tapered groove 50.

Figure 3:
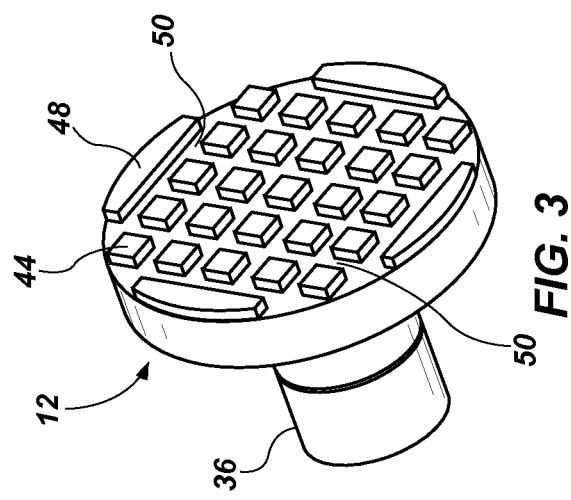
FIG. 3 is a perspective view of the embodiment of FIG. 1A.

The plurality of tapered grooves can result in a variety of geometric shapes when seen on the grooved face 38. For example, in some embodiments such as those shown in FIGS. 1A, 1B, 3, and 4, the plurality of ridges and furrows appear as raised squares 44. In some embodiments, such as those shown in FIGS. 5A through 5C, the plurality of ridges appear as concentric circles. In some embodiments, the plurality of ridges and furrows can include those for making more than one geometric pattern. For example, a portion of the grooved face 38 may include concentric circles while another portion may include raised squares 44. In FIG. 3, the grooved face includes raised squares 44 and four oval-like shapes 48 on the perimeter of the grooved face 38. As can be appreciated by one of skill in this art therefore, a variety of shapes on the face of the substrate holding device.

Figure 5A:
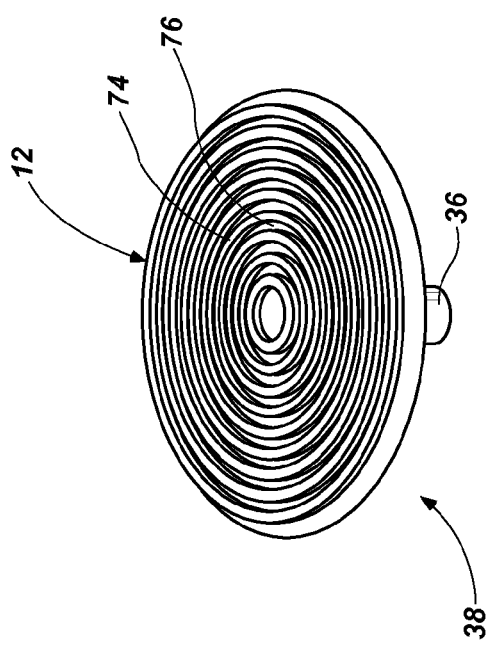
FIGS. 5A through 5C are perspective views of different embodiments of substrate holding devices having annular ridges and furrows.
Figure 5B:
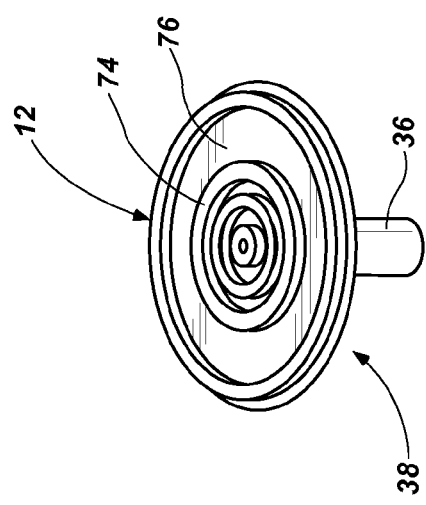
Figure 5C:
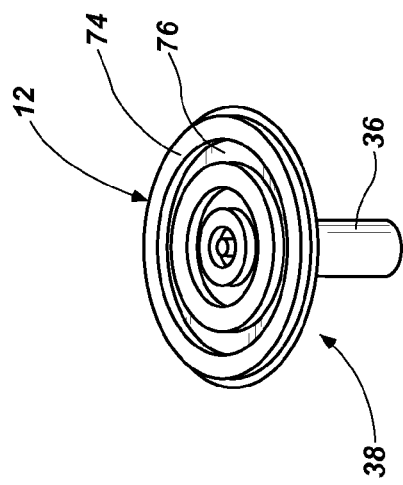

In some embodiments, the furrows have consistent widths as shown in the embodiments of FIGS. 3 and 1A for example. In some embodiments, the furrows have varying widths as shown in the embodiment of FIG. 5B. Moreover, the width of the respective ridges and furrows themselves can vary as shown in the embodiments of FIGS. 5A through 5C, provided that the resulting grooves have some taper to them.

In use for example, a surgeon excises a tissue specimen A from a patient. The operator then covers the substrate holding device 12 with embedding medium. The tissue sample A is then placed in the medium and may be frozen using a freezing agent. Alternatively, the mounted specimen A on the substrate holding device 12 may be placed in a cryostat for freezing. As the specimen A and mounting medium freezes, the plurality of tapered grooves 50 retain the specimen A onto the groove surface 38 of the substrate holding device 12.

As exemplified above, the substrate retaining device can be used in a variety of cryogenic techniques for pathological diagnosis and handling.

The invention claimed is:

1. A substrate holding device, comprising: a stem and a grooved face having a plurality of ridges and furrows forming tapered grooves;
    a plurality of tapered edges wherein each tapered edge is between a ridge and an adjoining furrow;
    a plurality of nontapered edges wherein each nontapered edge is between a ridge and an adjoining furrow;
    wherein each furrow adjoins a first adjacent ridge by a tapered edge and a second adjacent ridge by a tapered edge.

2. The substrate holding device of claim 1, wherein each furrow adjoins an adjacent ridge by a tapered edge.

3. A substrate holding device, comprising: a stem and a grooved face having a plurality of tapered grooves wherein each tapered groove further comprises a furrow adjoining first and second ridges;
    and wherein the width of the tapered groove at the top of the first and second ridges adjoining a furrow is less than the width of the tapered groove in the bottom of the furrow.

4. A substrate holding device for retaining frozen tissue samples, comprising: a stem and a tissue mounting face perpendicular to the stem, the tissue mounting face further comprising a plurality of tapered grooves configured to retain a mounting medium;
    and wherein the grooves are tapered to be wider at the bottom of the groove than the width of the top of the groove.

5. The substrate holding device of claim 4, wherein the mounting medium is a solid when cooled to a temperature less than 0° C.

6. The substrate holding device of claim 4, wherein the plurality of grooves form concentric circles.

7. The substrate holding device of claim 4, wherein the plurality of grooves are parallel to one another.

8. The substrate holding device of claim 4, wherein at least some of the plurality of grooves are perpendicular to other grooves.

9. The substrate holding device of claim 4, wherein the stem is of the form selected from the group consisting of: round, square, and rectangle.

10. The substrate holding device of claim 1, wherein the plurality of grooves form concentric circles.

11. The substrate holding device of claim 1, wherein the plurality of grooves are parallel to one another.

12. The substrate holding device of claim 1, wherein at least some of the plurality of grooves are perpendicular to other grooves.

13. The substrate holding device of claim 2, wherein the plurality of grooves form concentric circles.

14. The substrate holding device of claim 2, wherein the plurality of grooves are parallel to one another.

15. The substrate holding device of claim 2, wherein at least some of the plurality of grooves are perpendicular to other grooves.

16. The substrate holding device of claim 3, wherein the plurality of grooves form concentric circles.

17. The substrate holding device of claim 3, wherein the plurality of grooves are parallel to one another.

18. The substrate holding device of claim 3, wherein at least some of the plurality of grooves are perpendicular to other grooves.

* * * * *